(12) United States Patent
Weese et al.

(10) Patent No.: US 12,023,518 B2
(45) Date of Patent: Jul. 2, 2024

(54) RADIATION THERAPY PLANNING

(71) Applicant: KONINKLIJKE PHILIPS N.V., Eindhoven (NL)

(72) Inventors: Rolf Juergen Weese, Norderstedt (DE); Alfonso Agatino Isola, Eindhoven (NL); Maria Luiza Bondar, Waalre (NL); Torbjoern Vik, Hamburg (DE); Nick Flaeschner, Hamburg (DE); Jens Wiegert, Aachen (DE); Harald Sepp Heese, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 378 days.

(21) Appl. No.: 17/551,642

(22) Filed: Dec. 15, 2021

(65) Prior Publication Data
US 2022/0193448 A1 Jun. 23, 2022

(30) Foreign Application Priority Data
Dec. 18, 2020 (EP) .................................... 20215273

(51) Int. Cl.
*A61N 5/10* (2006.01)
(52) U.S. Cl.
CPC ......... *A61N 5/1038* (2013.01); *A61N 5/1048* (2013.01)
(58) Field of Classification Search
CPC .. A61N 5/1038; A61N 5/1048; A61N 5/1045; A61N 5/1047; A61N 5/1031;
(Continued)

(56) References Cited

U.S. PATENT DOCUMENTS

| 5,373,844 | A | 12/1994 | Smith |
| 2019/0083814 | A1 | 3/2019 | Tallinen |

(Continued)

FOREIGN PATENT DOCUMENTS

| WO | 2012024448 A2 | 2/2012 |
| WO | 2016092441 A1 | 6/2016 |

OTHER PUBLICATIONS

Fan, Jiawei et al, "Automatic treatment planning based on three-dimensional dose distribution predicted from deep learning technique", Medical Physics 2019, vol. 46 (1), pp. 370-381.
(Continued)

*Primary Examiner* — Kiet T Nguyen
(74) *Attorney, Agent, or Firm* — Sherry Austin

(57) ABSTRACT

The invention relates a system for assisting in planning a radiation therapy treatment provided using a treatment plan comprising irradiation parameters for controlling a delivery of radiation. The system is configured to (i) receive a first dose distribution, (ii) obtain a first objective function, which depends upon at least one parameter and a dose distribution, (iii) determine a first value of the parameter such that the first objective function fulfills a predefined criterion when being evaluated for the first value of the parameter and for a second dose distribution derived from the first dose distribution, (iii) provide the first objective function in connection with the first value of the at least one parameter to a user for modifying the first objective function to generate a second objective function, and (v) determine the treatment plan using the second objective function. Further, the invention relates to a corresponding method and computer program.

13 Claims, 1 Drawing Sheet

(58) Field of Classification Search
CPC .............. A61N 5/103; A61N 5/1049; A61N 2005/1055; A61N 2005/1061; A61N 2005/1092
USPC ..................................................... 250/492.3
See application file for complete search history.

(56) References Cited

U.S. PATENT DOCUMENTS

2019/0388708 A1* 12/2019 Kumar ................ A61N 5/1031
2020/0101317 A1 4/2020 Koponen

OTHER PUBLICATIONS

Babier, Aaron et al "Inverse optimization of objective function weights for treatment planning using clinical dose-volume histograms", Physics in Medical Biology, 2018, vol. 63, 105004.

Mahmood, Rafid et al "Automated Treatment Planning in Radiation Therapy using Generative Adversarial Networks", Proceedings of Machine Learning Research, 2018, vol. 85, pp. 1-15.

Nguyen, Dan et al, "A feasibility study for predicting optimal radiation therapy dose distributions of prostate cancer patients from patient anatomy using deep learning", Scientific Reports, 2019, 9, 1076.

Barragán-Montero, Ana Maria "Three-Dimensional Dose Prediction for Lung IMRT Patients with Deep Neural Networks: Robust Learning from Heterogeneous Beam Configurations", Medical Physics, vol. 46, No. 8, Aug. 2019.

Nguyen, Dan et al "Incorporating Human and Learned Domain Knowledge into Training Deep Neural Networks: A Differentiable Dose Volume Histogram and Adversarial Inspired Framework for Generating Pareto Optimal Dose Distributions in Radiation Therapy", Medical Physics, 2019.

Bortfeld, T. et al "Decomposition of pencil beam kernels for fast dose calculations in three-dimensional treatment planning", Medical Physics, vol. 20, No. 2, 1993.

McNutt, T.R. et al "Modeling Dose Distributions from Portal Dose Images using the Convolution/Superposition Method", Medical Physics, vol. 23, No. 82, 1996.

* cited by examiner

RADIATION THERAPY PLANNING

FIELD OF THE INVENTION

The invention relates to the planning of a radiation therapy treatment of a body region of a patient. More specifically, the invention is related to a method and a system for assisting in planning a radiation therapy treatment of a body region of a patient, wherein the treatment is provided on the basis of a treatment plan comprising irradiation parameters for controlling a delivery of radiation to the body region.

BACKGROUND OF THE INVENTION

In radiation therapy, ionizing radiation is applied to body regions of patients in order to control growth of or kill cancer cells in a target structure, such as a tumor, included in these body regions. In modern types of radiation therapy, such as so-called intensity-modulated radiation therapy (IMRT), radiation is delivered to the relevant body regions in accordance with inhomogeneous dose distributions, which determined such that a sufficiently high radiation dose is applied to the target structure, while sensitive structures in the vicinity of the target structure, which are usually also referred to as organs at risk (OARs), are spared as far as possible.

Such radiation doses distributions are particularly achieved by means radiation sources equipped with so-called multi-leaf collimators (MLCs) comprising leaves, which are independently moved in and out of the path of a radiation beam in order to shape it and vary its intensity across its cross section. Using such an MLC, the radiation can be applied in accordance with several IMRT modalities. For instance, known IMRT modalities include a so-called step-and-shoot approach in which radiation is delivered in several so-called segments, where each segment corresponds to a specific beam configuration including a specific position of the radiation source with respect to the patient and a specific MLC configuration and where no radiation is applied while changing from one segment to the next. In accordance with a further IMRT modality known as Volumetric Modulated Arc Therapy (VMAT), the radiation is delivered while the MLC and/or the radiation source are in constant motion. Hereby, treatment time can be reduced and it is generally possible to achieve dose distribution with improved coverage of the target structure and better sparing of OARs. In particular, the radiation source may be moved around the patient in one or more arcs.

In order to deliver the radiation to the relevant body region in accordance with a selected IMRT modality, the treatment devices are controlled based on irradiation parameters, such as parameters specifying the intensity of the radiation beams generated by the radiation source, the MLC configurations and the positions of the radiation source. The irradiation parameters are specified in a treatment plan, which is usually generated individually for treatment of a new patient—herein below also referred to as "patient of the day"—in a planning procedure.

More specifically, the treatment plans are often generated in an inverse planning procedure. In such a procedure, the target structure and the surrounding OARs are identified and treatment goals are defined based on the clinical prescription for the patient, which specify requirements for the radiation dose delivered to the target structure and to the OARs. Then, an optimization problem is formulated on the basis of the treatment goals taking into consideration the physical and technical constraints resulting from the treatment device and the IMRT modality to be used, and the optimization problem is solved in order to find a treatment plan resulting in a dose distribution that fulfills the specified treatment goals.

The optimization problem may particularly be solved in operator-guided iterative optimization procedure in several iteration cycles. In each cycle, the planner may review the generated treatment plan in order to check whether he/she is satisfied with the dose distribution resulting from the respective treatment plan. If not, the planner may make modifications to the optimization problem to achieve a desired dose distribution, and the next optimization cycle is carried out on the basis of the modified optimization problem.

The solution of the optimization problem typically involves an at least approximate minimization of an objective function, which is generated on the basis of the treatment goals for the patient. The objection function may be configured as a weighted sum of individual objective functions, where each individual objection function represents one objective to be fulfilled by the dose distribution delivered to the patient and is included into the overall objective function in accordance with an associated weight. The individual objective functions are typically generated using a physical model describing the absorption of the energy deposited in the tissue of the relevant body region by the radiation beam generated in accordance with the treatment parameters so that the objective function corresponds to an equation for these parameters. Further, the objectives and related objective functions are particularly determined based on the treatment goals. For instance, the objectives may require a certain minimum radiation dose to be delivered to the target structure and/or a certain maximum dose to be delivered to an OAR. The relative weights of the individual objective functions influence the likelihood for the related objectives to be fulfilled, particularly in case of conflicting objectives so that the individual objective functions relating to more important objectives are provided with a higher relative weight.

In each cycle of the optimization procedure, the objection function may be automatically minimized at least approximately, e.g. using a suitable numerical procedure. When the planner is not satisfied with the dose distribution resulting from the minimized objective function in one cycle, he/she may modify the optimization problem by modifying the individual objective functions and/or their weights. Such a modification may include the deletion of objective functions, the addition of new individual objective functions and/or the modification of weights of individual functions included in the overall objective function. Then, the modified objective function is at least approximately minimized in order to determine new treatment parameters corresponding to a new dose distribution.

In accordance with a new approach recently suggested for treatment planning, a dose distribution for the treatment of a patient is predicted by means of an artificial intelligence (AI) algorithm, as e.g. described in the publication J. Fan et al., "Automatic treatment planning based on three-dimensional dose distribution predicted from deep learning technique", Med. Phys. 2019, 46, 370-381. The AI algorithm may be trained using dose distributions, which have been delivered successfully to patients in the past, and the related anatomical configurations of the treated body regions of these patients. On the basis of the anatomical configuration of the patient of the day, the trained AI algorithm may then be capable of predicting a dose distribution to be delivered to this patient. Then, an objective function based on the difference between the predicted dose distributions and the dose distribution to be delivered is created for automatically generating the treatment plan.

Using this approach, clinical acceptable dose distributions and treatments plans can be generated efficiently in many cases. However, it would be desirable to allow a planner to review and modify the treatment plan.

In particular, this would be desirable if the dose distribution necessarily has to be modified in order to be delivered to the patient. This is the case when the dose distribution determined by the AI algorithm cannot be delivered to the patient, e.g. due to physical constraints or technical constraints of the IMRT modality applied in the treatment or the treatment device. For instance, such technical constraints may be violated if the AI algorithm is trained on the basis of dose distribution which have been delivered using treatment devices and/or IMRT modalities which differ from those used for the treatment of the patient of the day.

Moreover, the dose distribution determined by the AI algorithm may not be optimal for other reasons and in such cases, it may be possible to improve the dose distribution by means of a manual modification carried out by a planner.

SUMMARY OF THE INVENTION

It is an object of the invention to allow for a generation of a treatment plan for a radiation therapy treatment on the basis of a previously generated dose distribution such that a planner can control the generation of the treatment plan. In particular, it is an object of the invention to allow a planner to control the generation of a treatment plan on the basis of a dose distribution determined by an AI algorithm.

In accordance with one aspect, the invention suggests a system for assisting in planning a radiation therapy treatment of a body region of a patient, wherein the treatment is provided on the basis of a treatment plan comprising irradiation parameters for controlling a delivery of radiation to the body region. The system is configured to (i) receive a first dose distribution for the body region, (ii) obtain a first objective function, which depends upon at least one parameter and upon a dose distribution in the body region, (iii) determining a first value of the at least one parameter such that the first objective function fulfills a predefined criterion when being evaluated for the first value of the at least one parameter and for a second dose distribution derived from the first dose distribution, (iv) provide the first objective function in connection with the first value of the at least one parameter to a user for modifying the first objective function to generate a second objective function, and (v) determine the treatment plan using the second objective function. The predefined criterion may particularly require that the first objective function is at least approximately minimal.

Since the system produces a first objective function by determining the at least one parameter thereof based on a second dose distribution corresponding to the first dose distribution, it is possible to determine a treatment plan resulting in a modified dose distribution based on a modified second objective function. Hereby, it is possible to generate the treatment plan on the basis of the first dose distribution and to allow a planner to control the generation of the treatment plan by modifying the first objective function. Thus, a planner can control the generation of the treatment plan in accordance with the known planning procedure described above.

The system may be configured to generate the first dose distribution by means of an algorithm using artificial intelligence, particularly by means of a neural network. In this embodiment, the planner can generate a treatment plan on the basis of a dose distribution generated by means of an AI algorithm. Since such algorithms often produce acceptable results, a dose distribution generated by such an algorithm is a good starting point for the generation of a treatment plan under the control of a planner, which may allow for a fast and efficient generation of an optimized treatment plan.

In one embodiment, the system is configured to derive the second dose distribution by approximating the first radiation distribution as a function of beam elements to be applied in the treatment using a physical model describing the radiation absorbed in the body region of the patient depending upon the beam elements. The use of the physical model ensures that the second dose distribution is a feasible dose distribution that can actually be delivered to the patient. This is not necessarily true for the first dose distribution, particularly in case the first dose distribution is generated by means of an AI algorithm. In case the first dose distribution is not feasible, the second dose distribution will differ from the first dose distribution. However, if the first dose distribution can actually be delivered, the second dose distribution will essentially correspond to the first dose distribution.

In a related embodiment, the physical model is a linear model describing the radiation dose absorbed in the body region as a product of an influence matrix with a vector of beam elements. Such an influence matrix is known to the skilled person as such and may particularly specify the amount of dose absorbed by each of the volume elements—which are also referred to as voxels herein—from unit radiation intensity of each of the beam elements.

In a further embodiment, the system is configured to derive the second dose distribution based on a template specifying possible beam elements for a treatment mode selected for the radiation treatment. This allows for considering only those beam elements, which can be delivered during the treatment in accordance with the selected treatment mode and ensures that the second dose distribution is feasible in the selected treatment mode.

The treatment mode may particularly correspond to an IMRT modality, which may be selected among a treatment according to the step-and-shoot approach and a VMAT treatment. Therefore, one embodiment of the invention includes that the template is selected from a plurality of templates on the basis of a modality of the treatment, the modality of the treatment being selected from a group at least comprising step-and-shoot IMRT and VMAT.

In further embodiments, there may be several templates for a treatment according to the step-and-shoot approach and/or several templates for a VMAT treatment and the template is further selected on the basis of additional information about the treatment mode. For a treatment according to the step-and-shoot approach, there particularly be templates for different numbers of segments and the template may be selected based on the number of segments to be delivered during the treatment. For a VMAT treatment, there may be templates for different numbers of arcs and the template may be selected based on the number of arcs to be delivered during the treatment.

In a further embodiment of the invention, the system is configured to derive the second dose distribution by minimizing a third objective function, which depends on a difference between the first and the second dose distribution. In this embodiment, the system determines the second dose distribution such that the third objective function is minimized.

In a related embodiment, elements of the first and second dose distribution are provided with different weights in the third objective function, the weights being selected based on the parts of the body region to which the elements of the first and second dose distribution belong. In particular, each difference between an element of the first dose distribution and a corresponding element of the second dose distribution may be provided with an associated weight. In case of differences between the second dose distribution and the first dose distribution, the weights ensure that the differences will be smaller in parts to which a higher weight is allocated. Such parts may particularly correspond to the target structure of the treatment and/or to the OARs.

In one embodiment of the invention, the first objective function includes a sum of individual objective functions entering into the first objective function with an associated weight and wherein the at least one parameter is at least one of the weights. Each of the individual objective functions represents a requirement of the radiation to be delivered to a part of the body region during the treatment. Related examples include individual objective functions representing a requirement that a radiation dose delivered to a part of the body region, such as the target region, is higher than a minimum dose and a requirement that a radiation dose delivered to a part of the body region, such as an OAR, is lower than a maximum dose.

In a related embodiment, the second objective function is derived from the first objective function by a modification from a group comprising a modification of at least one of the weights, an addition to an individual objective function to the objective function and a deletion of an individual objective function. Particularly using these modifications, the planner may determine a treatment plan corresponding to a certain optimized dose distribution including changes relative to the second dose distribution.

In a further aspect, the invention suggests a method for assisting in planning a radiation therapy treatment of a body region of a patient, wherein the treatment is provided on the basis of a treatment plan comprising irradiation parameters for controlling a delivery of radiation to the body region. The method comprises (i) receiving a first dose distribution for the body region, (ii) obtaining a first objective function, which depends upon at least one parameter and on a dose distribution in the body region, (iii) determining a first value of the at least one parameter such that the first objective function fulfills a predefined criterion when being evaluated for the first value of the at least one parameter and for a second dose distribution derived from the first dose distribution, (iv) providing the first objective function in connection with the first value of the at least one parameter to a user for modifying the first objective function to generate a second objective function, and (v) determining the treatment plan using the second objective function.

In a further aspect, the invention suggests a computer program comprising program code for instructing a computer to perform the method, when the program code is executed in the computer.

It shall be understood that the system of claim 1, the method of claim 12 and the computer program of claim 13 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings.

DETAILED DESCRIPTION OF EMBODIMENTS

Figure 1:
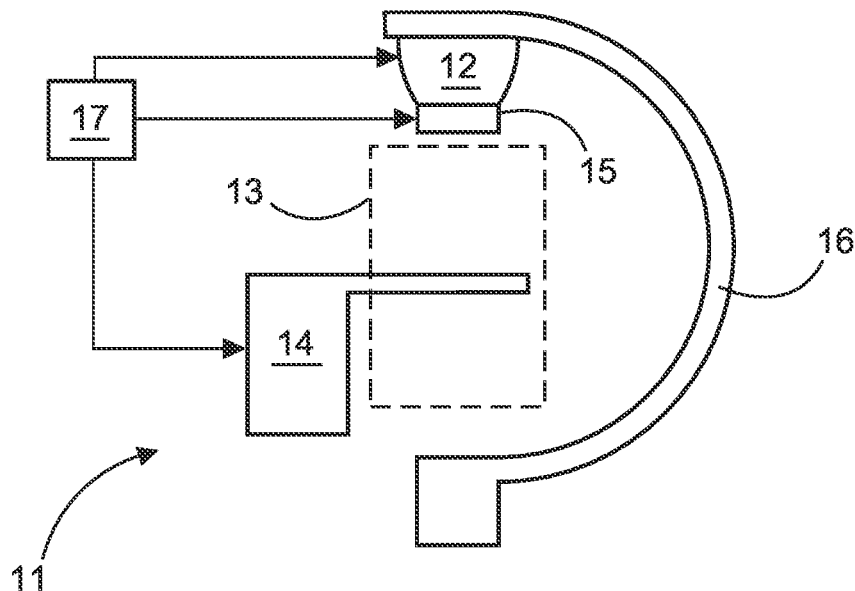
FIG. 1 schematically and exemplarily shows components of a radiation therapy system for delivering a radiation therapy treatment to patients, and
FIG. 2 schematically and exemplarily shows components of a planning system for planning a radiation therapy treatment.

FIG. 1 schematically and exemplarily illustrates an embodiment of a radiation therapy (RT) system 11 for delivering IMRT treatments to tumors or other diseased target structures within a human or animal patient body. In the illustrated embodiment, the RT system 11 comprises a radiation source 12, which can be operated to emit ionizing radiation to be delivered to a region of the patient body including the target structure. In order to deliver the radiation, the patient body is positioned in a treatment zone 13 of the system on a moveable patient table 14.

The radiation source 12 may include an x-ray tube or a linear particle accelerator for producing ionizing radiation. The radiation source 12 is controllable in order to vary the intensity and/or energy of the generated radiation. Further, the radiation source 11 may be provided with a collimator 15 for shaping the radiation beam. The collimator 15 may particularly allow varying the radiation intensity across the cross section of radiation beam in a defined way. For this purpose, the collimator 15 may be configured as multi-leaf collimator (MLC). The collimator 15 is preferably likewise controllable to change the shape of the radiation beam during the treatment.

Further, the relative position of the radiation source 12 with respect to the body or target structure can be varied in order to change the position at which the radiation beam enters the body surface and/or the angle under which the beam enters the body. For this purpose, the radiation source 12 may be mounted on rotatable gantry 16 so that the radiation source 12 can be rotated around the treatment zone 13 and, thus, around the patient table 14 within a certain angular range, which may be 360° or less. For instance, the gantry 16 may include a C-arm carrying the radiation source 12. In addition, the radiation source 12, the gantry 16 and/or the patient table 14 may be movable back and forth in a direction parallel to the rotation axis of the gantry 16. Moreover, it may also be possible to rotate the patient table 14 around an axis perpendicular to the rotation axis of the gantry 16.

The RT system 11 may be capable of delivering the IMRT treatments in accordance with one or more IMRT modalities. In one embodiment, the RT system 11 is configured to deliver radiation to a patient in accordance with VMAT procedures. In addition or as an alternative, the RT system may be configured to deliver radiation in a step-and-shoot approach. In VMAT, the radiation is delivered while the MLC 15 and/or the radiation source 12 are in constant motion. Typically, the radiation source 12 is rotated around the patient in one or several arcs during a VMAT treatment. In accordance with the step-and-shoot approach the radiation is delivered in separate segments, where each segment corresponds to a specific beam configuration including a specific position and orientation of the radiation source 11 with respect to the patient and a specific configuration of the MLC 15 and where the radiation source 12 is turned off while changing from one segment to the next. These IMRT modalities are known to the skilled person as such so that further details about these modalities do not have to be provided here.

For controlling the components of the RT system 11 including the radiation source 11, the collimator 15, gantry 16 and the patient table 14, to deliver a radiation therapy treatment in accordance with one of the aforementioned IMRT modalities, the RT system 11 includes a control unit 17. Preferably, the control unit 16 is implemented in a processor unit including a microprocessor for executing a software program comprising the control routines carried out by the control unit 17.

During the RT treatment of a patient, the control unit 17 controls the RT system on the basis of a treatment plan, which specifies the irradiation parameters to be used for the treatment. These parameters may particularly specify the energy of the radiation generated by the radiation source 12, the configuration of the MLC 15, the position of the gantry 16 and/or the position of the patient table 14. When the RT treatment is delivered in accordance with a step-and-shoot approach, the treatment specifies the irradiation parameters for each segment. In case of a VMAT treatment, the treatment plan specifies the irradiation parameters for a plurality of so-called control points. During the treatment, the control unit 17 controls the RT system 11 to consecutively apply the irradiation parameters of these control points, where the radiation is continuously applied also when changing the irradiation parameters from one control point to the next.

Figure 2:
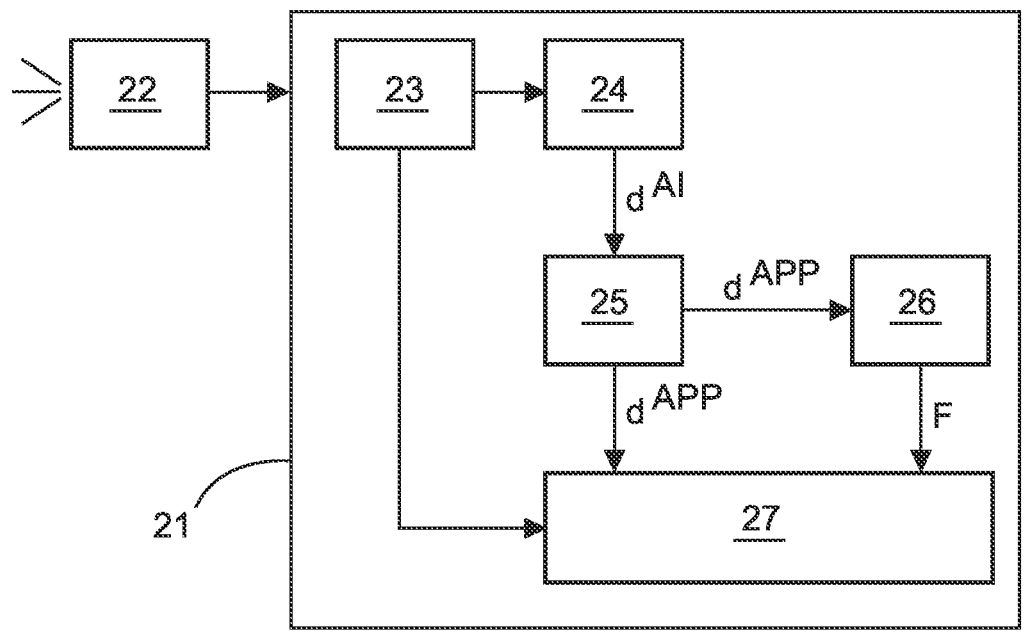

The treatment plan for the treatment of a particularly patient—herein also referred to as "patient of the day"—is individually generated using a planning system 21. In the following, embodiments of the planning system 21 will be described making reference to FIG. 2, which schematically shows components of the planning system 21 in exemplary embodiments. The planning system may be implemented as a computer comprising at least one microprocessor for executing a computer program providing routines for generating a treatment plan as described herein below. The components of the planning system 21 illustrated in FIG. 2 may particularly correspond to modules of the computer program.

The treatment plan is generated on the basis of a three-dimensional image of the body region of the patient, which includes the target structure to be treated and which is also referred to as planning image herein. Therefore, the planning procedure starts with an acquisition of the planning image and the delineation of the relevant anatomical structures in a delineation unit 23 of the planning system 21. The planning image is acquired by means of an imaging unit 22 using any suitable imaging, such as, for example, computed tomography (CT) imaging or magnetic resonance (MR) imaging. In embodiments, the planning image may also result of a fusion of several images acquired using different imaging modalities. In the process of delineating the relevant anatomical structures, the contours of the target structure and of any OARs in the vicinity of the target structure are determined in a delineation unit 23 and stored for the further planning procedure. For this purpose, a binary mask may be created and stored the target structure and for each OAR. The delineation may be carried in out in an automatic or in an operator-assisted procedure, as known in the art as such.

In the next step, a first dose distribution for the treatment of the patient is determined on the basis of the contours of the target structure and the OARs. In one embodiment, the first dose distribution is automatically determined by an AI algorithm performed in an AI unit 24 of the planning system.

In embodiments, the AI algorithm may be performed by a neural network, which may be a convolutional neural network (CNN), such as a U-net model. The neural network may be trained using data including dose distributions delivered to the relevant body region of other patients in the past. Upon the training, the neural network may predict the dose distribution on the basis of anatomical structure of the relevant region of the patient body as represented by the planning image and the contours of the target structure and the OARs identified therein. In addition, the neural network may optionally also predict the dose distribution on the basis of information about the beam configuration, such as, for example, the number of segments and the and the position of the radiation source 11, particularly the angle of the gantry 16, in case of a treatment according to the step-and-shoot approach and the number of arcs in case of a VMAT treatment. Examples of AI algorithms, which are performed by a neural network and which may be carried out in the AI unit 24 are described in J. Fan et al., "*Automatic treatment planning based on three-dimensional dose distribution predicted from deep learning technique*", Med. Phys. 2019, 46, 370-381; A. M. Barragán-Montero et al., "*Three-Dimensional Dose Prediction for Lung IMRT Patients with Deep Neural Networks: Robust Learning from Heterogeneous Beam Configurations*", arXiv:1812.06934; D. Nguyen et al., "*A feasibility study for predicting optimal radiation therapy dose distributions of prostate cancer patients from patient anatomy using deep learning*", Scientific Reports 2019, 9, 1076.

Using the first dose distribution generated in the AI unit 24, the treatment plan is further generated based on a physical model describing the radiation dose absorbed in the irradiated body region of the patient as a function of the incident radiation generated by means of the RT system 11. For this purpose, the radiation incident into the body region may be modelled as a collection of beam elements as it is known as such to a person skilled in the art. The beam elements—which are also referred to as beamlets or bixels—correspond to small portions of the radiation beam which result from a partitioning of the beam's cross section into portions in which the intensity can be controlled individually using the MLC 15.

In the present planning procedure, beam elements of the radiation beam are considered for a set of segments of a treatment according to the step-and-shoot approach or a set of control points of a treatment according to the VMAT approach on the basis of a template, which is selected from a plurality of templates stored in the planning system. Each template specifies the beam elements, which can be delivered during the treatment. In the planning system 21, one or more templates for a treatment according to the step-and-shoot approach and one or more templates for a VMAT treatment may be available. Each template for a treatment according to the step-and-shoot approach may specify one or more parameters of the group including the number of segments, the position of the radiation source 11 and more particularly the angle of gantry 16 in each segment, the maximum number of beamlets per segment and/or the minimum area of the cross section of the beamlets and the minimum radiation intensity per beamlet (e.g. specific in monitor units). For instance, there may be templates including 2-14 segments and related positions of the radiations source 12 in each of the segments. Each template for a VMAT treatment may specify the number of arcs, the angular range of movement for each arc, the number of control points per arc and/or the angular distance between the positions of the radiation source 12 at the control points.

From the available templates, the approximation unit 24 selects a specific template for modelling the incident radiation during the treatment. Thus, depending on whether the treatment is to be delivered in accordance with the step-and-shoot approach or in accordance with the VMAT approach, the selection is made among the templates for the relevant approach. From these templates, a specific template may be selected in an automatic or operator-guide procedure in which the template is selected by the planner. The latter approach may be preferred since the planner can usually select a more appropriate template on the basis of his/her experience.

As said, the selected template specifies the beamlets, which are available for delivery during the treatment. Moreover, since the beam elements are controlled by variations of the configuration of the MLC 15, there are certain relationships between different beam elements. The MLC 15 obscures beam elements by moving leaves into the radiation path of the beam element. This means that an obscuration of a beam element in the inner of the radiation beam is usually connected with an obscuration of other beam elements through which the relevant MLC leaf has to be moved in order to obscure the beam elements. In the planning procedure, these relationships between the beam elements may be considered as constraints, which have to be fulfilled by the beam elements delivered during the treatment.

The beam elements for all possible positions during the treatment are also referred to as fluence map. In order to carry out the planning procedure, these beam elements may be included in a high-dimensional fluence vector b, where each component $b_j$ of the fluence vector b corresponds to the fluence value of the beam element j, which corresponds to a certain portion of the cross-section of the radiation beam at a certain position of the radiation source 12.

In order to describe the radiation dose absorbed in the irradiated body region of the patient as a function of the beam elements, a linear physical model may be applied. In accordance with such a model, the dose distribution in the irradiated body region is determined by multiplying the fluence vector b with an influence matrix P. This means that a dose vector d is determined according to $$d = P \cdot b$$

Each component $d_i$ of the dose vector d specifies the radiation dose absorbed by a voxel i of the irradiated body region, where such volume elements are often also referred to as voxels. Each component $P_{ij}$ of the influence matrix P quantifies the amount of dose absorbed by the voxel i per unit fluence from the beamlet j.

The influence matrix P is a function of the anatomical configuration of the irradiated body region of the patient. In principle, the influence matrix P can be calculated by means of a ray tracing for all beamlets, where the deposited energies are estimated for the voxels included in the ray paths in accordance with their physical properties with respect to the interaction with the radiation. These properties can particularly be quantified using the mass attenuation coefficient.

For calculating the influence matrix, any procedure known to a person skilled in the art can be used. For examples, approaches for calculating the influence matrix are described in T. Bortfeld, W. Schlegel, B. Rhein, "*Decomposition of pencil beam kernels for fast dose calculations in three-dimensional treatment planning*" Med. Phys., 20(2), 311 (1993), and in T. R. McNutt, T. R. Mackie, Paul Reckwerdt, and Bhudatt R. Paliwal, "*Modeling Dose Distributions from Portal Dose Images using the Convolution/Superposition Method*", Med. Phys. 1996; 23-28, as well as in other works of T. R. Mackie. Further, algorithms for calculating the influence matrix are also implemented in commercially available treatment planning software, such as the software "Pinnacle[3]" by Philips.

Using the aforementioned linear model with an influence matrix P determined for the patient of the day, the first dose distribution determined by the AI unit may be approximated to obtain a second dose distribution, which is a product of the influence matrix P with a fluence vector b corresponding to the selected template.

In this procedure, also the aforementioned constraints of the beam elements delivered during the treatment are considered. Thus, the obtained second dose distribution is configured such that it can actually be achieved during the treatment. As said, this is not necessarily the case for the first dose distribution. However, if the first dose distribution can be achieved during the treatment, the second dose distribution is generally identical to the first radiation distribution.

In order to approximate the first dose distribution, the approximation unit 25 may minimize an objective function, which depends on the difference between the first and second dose distribution. Further, the objective function may include weights such that parts of the relevant body region of the patient are assessed with a higher weight. In case the approximated second dose distribution differs from the first dose distribution, the differences will be smaller in parts to which a higher weight is allocated. Thus, the weighting ensures that the second radiation dose well corresponds to the first dose distribution in part of the body region having a higher associated weight. Such parts may correspond to the target structure of the treatment and/or to the OARs.

In one embodiment, the approximation unit 25 minimizes an objective function $O_1$ of the form $$O(b) = \Sigma_i a_i [d_i^{AI} - (Pb)_i] + R(b)$$

where $d_i^{AI}$ represents the value of the first dose distribution $d^{AI}$ for the voxel i, $(Pb)_i$ is the value of the product Pb for the voxel i, $a_i$ is the weight associated with the voxel i and R(b) is a regularization term.

In this function, the weights $a_i$ may be specified individually for each pixel. However, as said above, the same weight $a_i$ is advantageously selected for voxels i belonging to a certain part of the relevant region of the patient body, such as the target structure and/or the OARs. In one specific example, the weights $a_i$ are set to 1 for the target structure and the OARs and they are set to 0 for all other parts of the body region.

The regularization term R(b) is particularly included into the objective function to prevent numerical instabilities, which might occur in view of radiation beams for two segments or control points having approximately the same or opposite directions and to prevent noise in the fluence map. Thus, the regularization term ensures that clinically acceptable smooth fluence maps are generated. In one embodiment, the regularization term may be given by $$R(b) = \alpha \cdot b^2$$

with a suitably selected constant $\alpha$. However, in further embodiments, other regularization terms may be used.

The approximation unit 25 minimizes the objective function subject to the condition that the components $b_i$ of the fluence vector b are equal to or greater than zero and subject to the aforementioned constraints of the fluence vector resulting from the relationships between the beamlets $b_i$ due to their realization by means of the MLC 15. As a result of the minimization, the approximation unit 25 determines a fluence vector $$b^{app} = \arg\min O(b)$$

and the second dose distribution, which is also denoted as $d^{app}$ herein and which is given by $$d^{app} = P \cdot b^{app}.$$

Using the second dose distribution, a determination unit 26 determines a further objective function corresponding to those which are often used in treatment planning, particularly in so-called Fluence Map Optimization (FMO) in order to find a fluence vector to be used during the treatment.

In FMO, the treatment plan is found by determining a fluence vector resulting in an optimal dose distribution for the treatment of a patient. In order to determine the desired fluence vector, an objective function $$F(b) = F(d = P \cdot b)$$

may be minimized, which is produced on the basis of the prescribed dose objectives and which may be a weighted sum of individual objective functionals $f_k$ corresponding to the individual dose objectives. Thus, the objective function F may have the form $$F = \Sigma_{k=1}^{N} w_k \cdot f_k$$

where $w_k$ is the weight assigned to the individual objection function $f_k$ and N is the total number of individual dose objectives considered in the overall objective function F.

For example, these dose objectives may specify a minimum dose $d_{min}$ to be delivered to certain voxels, such as the voxels of the target structure, or a maximum dose $d_{max}$ to be delivered to certain voxels, such as the voxels of the OARs. Such objectives may be represented by piecewise quadratic cost function of the form $$f_k \sim \Sigma_i H(d_{min} - d_i)(d_{min} - d_i)^2$$

Or $$f_k \sim \Sigma_i H(d_i - d_{max})(d_i - d_{max})^2$$

where the sum is calculated over all voxels i of the volume to which the objective relates and $H(x)$ is the Heaviside function defined as $$H(x) = \begin{cases} 0, & x < 0 \\ 1, & x \geq 0 \end{cases}$$

A further example relates to a dose objectives requiring a uniform dose distribution in a certain volume, which may again correspond to the target structure or an OAR. Such an objective may be represented by an individual objective function of the form $$f_k \sim \Sigma_i (d_i - d_{avg})^2$$

where the sum is again calculated over the voxels i included in the relevant volume and where $d_{avg}$ denotes the average radiation dose absorbed in this volume.

In the determination unit 26, the objective function F is generated based on the treatment goals for the patient of the day, which are specified in the patient's clinical prescription. This can be done automatically or in an operator-guided procedure as known in the art as such. Typically, this process involves the generation of an objective function including individual objective function specifying a minimum dose objective relating to the target structure of the treatment and maximum dose objectives for the OARs. In addition, individual objective functions, such as individual objective functions relating to uniformity requirements for the radiation dose, may be included into the overall objective function.

The parameters of the individual objective functions, such as the minimum and maximum dose values may be determined based on the clinical prescription for the patient. In addition, such values may be determined based on the second dose distribution $d^{app}$ determined in the approximation unit 25. The second dose distribution may particularly be considered if a certain volume is subject to a maximum dose requirement, which is fulfilled in the second dose distribution. In this case, the maximum dose value for the individual objective function relating to this volume may be set to the smallest dose value that occurs in the volume according to the second dose distribution. This value may be smaller than the minimum dose specified in the patient's clinical requirement so that it may be possible to over-fulfill the clinical prescription. Similarly, the second dose distribution may particularly be considered if a certain volume is subject to a minimum dose requirement, which is fulfilled in the second dose distribution. If so, the minimum dose value for the individual objective function relating to this volume may be set to the largest dose value that occurs in the volume according to the second dose distribution. This value may be larger than the minimum dose specified in the clinical prescription for the patient so that this prescription may be over-fulfilled.

However, no values are initially specified for the weights $w_i$ associated with the individual objective functions included in the objective function in the process of generating this function in the determination unit 26. Rather, these weights are determined based on the second dose distribution $d^{app}$ determined in the approximation unit 25. More specifically, the weights are determined such that the objective function fulfills a predetermined criterion when being evaluated for the second dose distribution. In the embodiments described herein below, the weights are particularly determined such that the objective function is at least approximately minimal when being evaluated for the second dose distribution. This corresponds to the assumption that the second dose distribution is at least approximately an optimal solution of the optimization problem corresponding to the objective function.

When the objective function is approximately, this means that its derivatives with respect to the beamlets $b_j$ are at least approximately zero. Using the linear model for approximating the dose distribution as explained above, these derivatives are given by $$\frac{\partial F(b)}{\partial b_j} = \Sigma_{k=1}^{N} \Sigma_i w_k \cdot P_{i,j} \cdot \frac{\partial f_k}{\partial d_i}$$

In order to determine the weights, this expression can be evaluated for the second dose distribution $d^{app}$ and set to zero. This yields a set of linear equations for the weights $w_k$, which can be approximately solved using procedures known to a person skilled in the art.

In order to avoid trivial solutions in which all weights are equal to zero, one of the weights may be set to a predetermined value and the other weights might be constrained to be strictly positive. For instance, the weight $w_N$ may be set to 1. This results in a set of linear equations, which may be written as a matrix equation $$A \cdot w = y$$

where the components of the vector w correspond to the weights $w_k$ (k=1, ..., N−1), where the components $A_{jk}$ of the matrix A are given by $$A_{jk} = \Sigma_i P_{ij} \cdot \left. \frac{\partial f_k}{\partial d_i} \right|_{d=d^{app}}$$

and where the components $y_i$ of the vector y are given by $$y_j = \Sigma_i P_{ij} \cdot \left. \frac{\partial f_N}{\partial d_i} \right|_{d=d^{app}}$$

where the notation $g(x)|_{x=x0}$ specifies that a function g(x) is to be evaluated for x=x0.

In general, the set of linear equations will include more equations than weights $w_k$ to be determined so that it corresponds to a so-called overdetermined system of equations. For such a system of equations, a solution can be approximated using, for example, the method of least squares, which is known to the person skilled in the art as such. According to this method, the approximate solution is given by $$w = (A^T A)^{-1} A^T y$$

where the superscripts "T" and "−1" denote the transposed matrix and the inverse matrix. In one embodiment, the determination unit 26 determines the weights $w_k$ using this method and the aforementioned equation.

In a further embodiment, the determination unit 26 determines the weights $w_k$ such that the norm of the gradient of the objective function F with respect to the beamlets is zero or at least as small as possible, when evaluated for the second dose distribution and when the values of the weights $w_k$ are subject to one or more constraints. Thus, the weights $w_k$ are determined such that a cost function C, given by $$C(w) = \Sigma_j \left( \left. \frac{\partial F(b)}{\partial b_j} \right|_{d=d^{app}} \right)^2$$

is minimized, i.e. that the cost function C is at least approximately equal to zero. Particularly in order to avoid trivial solution, the cost function C is minimized while the weights $w_k$ are subject to predetermined constrains. For example, the weighs might be constrained to be strictly positive, one weight might be assigned to a predefined positive constant while the rest might be constrained to be strictly positive, the sum of the squared weights might be constrained to be equal to a predefined positive constant or the sum of weights might be constrained to be equal to a predefined positive constant.

The one or more constraint(s) to be applied may selected manually by the operator or they can be predetermined in the determination unit such that an appropriate non-trivial solution can be obtained. Taking into consideration the selected constraint(s), the cost function C can be minimized using any suitable numerical constrained optimization algorithm known to the person skilled in the art. Exemplary algorithms, which can be applied, are described in the text book J. Nocedal and S. Wright, "Numerical Optimization", Springer, 2006.

In a different embodiment, the definition of the functionals $f_k$ might be modified such that the value of the modified functionals at the second dose distribution $d^{app}$ is within predefined limits.

While the determination unit 26 determines the weights $w_k$ in the aforementioned embodiments, the determination unit 26 additionally determines further parameters of the objective function F. These parameters may particularly comprise the minimum and/or maximum dose values specified in the objective function. In related embodiments, these values are considered variable in addition to the weights $w_k$ and the determination unit 26 determines these values and the weights $w_k$ such that the objective function is approximately minimized when evaluated for the second dose distribution. For this purpose, a system of equations for determining the maximum and/or minimum dose values and the weights $w_k$ may be established based on the derivatives of the objective function with respect to the relevant dose values and the weights $w_k$, similar as described above in connection with the determination of the weights. The system of equations will be linear with respect to the weights $w_k$ and quadratic with respect to the minimum and/or maximum dose levels and can be solved using a suitable numerical algorithm.

In all embodiments of the determination unit 26 described above, the determination unit determines an objective function F which is approximately minimal when evaluated for the second dose distribution. This objective function F including the determined weights $w_k$ and, if applicable, the determined minimum and/or maxim dose values as well as the second dose distribution together with the related fluence map, the influence matrix and the planning images with the delineated target structure and OARs are provided to an optimization unit 27. In the optimization unit 27, a further optimized dose distribution and fluence map are determined based on the objective function and the second dose distribution in an iterative operator-guided procedure.

In each step of this procedure, the planner may review the current dose distribution. This review typically includes the evaluation of dose-volume histograms (DVHs) for the target structure and the OARs in order to determine whether the treatment goals for the patient can be fulfilled in the best possible way. If the planner is satisfied with the dose distribution determined in one step of the procedure, the treatment plan for the treatment of the patient is generated based on this dose distribution. This may be done by translating the fluence map that corresponds to the dose distribution into irradiation parameters for controlling the RT system 11 such that the fluences included in the map are delivered during the treatment. This translation can be done in a manner known to the person skilled in the art as such.

When the planner is not satisfied with the dose distribution, he/she may modify the objective function. Thereupon, a new dose distribution is determined which at least approximately minimizes the modified objective function and which is reviewed by the planner, as described above. Possible modifications of the objective function include a modification of one or more of the weights $w_k$ of the individual objective functions included in the overall objective function. Further modifications may include the deletion of one or more individual objective functions from the overall objective function and/or the addition of new individual objective functions to the overall objective function.

In such a way, the planner can further optimize the second dose distribution, which results from the first dose distribution determined in the AI unit 24 as described above.

Variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for assisting in planning a radiation therapy treatment of a body region of a patient, wherein the treatment is provided on the basis of a treatment plan comprising irradiation parameters for controlling a delivery of radiation to the body region, the system being configured to:
   receive a first dose distribution ($d^{AI}$) for the body region,
   obtain a first objective function (F), which depends upon at least one parameter and upon a dose distribution in the body region,
   determine a first value of the at least one parameter such that the first objective function (F) fulfills a predefined criterion when being evaluated for the first value of the at least one parameter and for a second dose distribution ($d^{app}$P) derived from the first dose distribution ($d^{AI}$),
   provide the first objective function (F) in connection with the first value of the at least one parameter to a user for modifying the first objective function (F) to generate a second objective function, and
   determine the treatment plan using the second objective function.

2. The system as defined in claim 1, configured to generate the first dose distribution ($d^{AI}$) is by means of an algorithm using artificial intelligence, particularly by means of a neural network.

3. The system as defined in claim 1, configured to derive the second dose distribution ($d^{app}$) by approximating the first dose distribution ($d^{AI}$) as a function of beam elements to be applied in the treatment using a physical model describing the radiation absorbed in the body region of the patient depending upon the beam elements.

4. The system as defined in claim 3, wherein the physical model is a linear model describing the radiation dose absorbed in the body region as a product of an influence matrix with a vector of beam elements.

5. The system as defined in claim 1, configured to derive the second dose distribution ($d^{app}$) based on a template specifying possible beam elements for a treatment mode selected for the treatment.

6. The system as defined in claim 5, wherein the template is selected from a plurality of templates on the basis of a modality of the treatment, the modality of the treatment being selected from a group at least comprising step-and-shoot intensity modulated radiation therapy, IMRT, and volumetric modulated arc therapy, VMAT.

7. The system as defined in claim 1, configured to derive the second dose distribution ($d^{app}$) by minimizing a third objective function, which depends on a difference between the first and the second dose distribution ($d^{AI}, d^{app}$).

8. The system as defined in claim 7, wherein elements of the first and second dose distribution ($d^{AI}, d^{app}$) are provided with different weights in the third objective function, the weights being selected based on the parts of the body region to which the elements of the first and second dose distribution ($d^{AI}, d^{app}$) belong.

9. The system as defined in claim 1, wherein the first objective function (F) includes a sum of individual objective functions entering into the first objective function with an associated weight and wherein the at least one parameter is at least one of the weights.

10. The system as defined in claim 9, wherein each of the individual objective functions represents a requirement of the radiation to be delivered to a part of the body region during the treatment.

11. The system as defined in claim 9, wherein the second objective function is derived from the first objective function by a modification from group comprising a modification of at least one of the weights, an addition of an individual objective function to the objective function and a deletion of an individual objective function.

12. A method for assisting in planning a radiation therapy treatment of a body region of a patient, wherein the treatment is provided on the basis of a treatment plan comprising irradiation parameters for controlling a delivery of radiation to the body region, the method comprising:
   receiving a first dose distribution ($d^{AI}$) for the body region,
   obtaining a first objective function (F), which depends upon at least one parameter and on a dose distribution in the body region,
   determining a first value of the at least one parameter such that the first objective function (F) fulfills a predefined criterion when being evaluated for the first value of the at least one parameter and for a second dose distribution ($d^{app}$) derived from the first dose distribution ($d^{AI}$),
   providing the first objective function (F) in connection with the first value of the at least one parameter to a user for modifying the first objective function (F) to generate a second objective function, and
   determining the treatment plan using the second objective function.

13. A computer program comprising program code for instructing a computer to perform a method as defined in claim 12, when the program code is executed in the computer.

* * * * *